US010874871B2

(12) United States Patent
Ginhoux et al.

(10) Patent No.: US 10,874,871 B2
(45) Date of Patent: Dec. 29, 2020

(54) MAGNETIC STIMULATION DEVICE COMPRISING A FORCE-SENSING RESISTOR

(71) Applicant: AXILUM ROBOTICS (SOCIETE PAR ACTIONS SIMPLIFIEE), Strasbourg (FR)

(72) Inventors: Romuald Ginhoux, Strasbourg (FR); Benjamin Maurin, Berstett (FR); Michel Berg, Rueil Malmaison (FR)

(73) Assignee: AXILUM ROBOTICS (SOCIETE PAR ACTIONS SIMPL, Strasbourg (FR)

( * ) Notice: Subject to any disclaimer, the term of this patent is extended or adjusted under 35 U.S.C. 154(b) by 367 days.

(21) Appl. No.: 15/767,052

(22) PCT Filed: Nov. 9, 2016

(86) PCT No.: PCT/EP2016/077152
§ 371 (c)(1),
(2) Date: Apr. 9, 2018

(87) PCT Pub. No.: WO2017/081087
PCT Pub. Date: May 18, 2017

(65) Prior Publication Data
US 2019/0060659 A1 Feb. 28, 2019

Related U.S. Application Data

(60) Provisional application No. 62/252,684, filed on Nov. 9, 2015.

(51) Int. Cl.
*A61N 2/02* (2006.01)
*G01L 1/22* (2006.01)
(Continued)

(52) U.S. Cl.
CPC ............ *A61N 2/02* (2013.01); *A61N 2/006* (2013.01); *B32B 3/08* (2013.01); *B32B 5/00* (2013.01);
(Continued)

(58) Field of Classification Search
CPC .................. A61N 2/006; A61N 2/02
See application file for complete search history.

(56) References Cited

U.S. PATENT DOCUMENTS 7,113,179 B2  9/2006  Baker et al.
8,177,702 B2  5/2012  Riehl et al.
(Continued)

FOREIGN PATENT DOCUMENTS

WO  2006/035143 A1  4/2006
WO  2014/100045 A1  6/2014

OTHER PUBLICATIONS

International Search Report, dated Jan. 19, 2017, from corresponding PCT/EP2016/077152 application.

*Primary Examiner* — Christine H Matthews
(74) *Attorney, Agent, or Firm* — Ipsilon USA, LLP

(57) ABSTRACT

Disclosed is an FSR sensor compatible with a magnetic stimulation coil and intended to be fixed to a magnetic stimulation coil and including: a first layer made of biocompatible flexible material intended to be applied to the skin of a patient; a second layer including a pattern or an area of force sensitive or resistive ink; a third layer including adhesive material, forming a peripheral spacer element; a fourth layer made of a flexible heat-stable polycarbonate substrate with a printed conductive pattern of a force sensing circuit; and a fifth layer forming an adhesive surface on the bottom face. The pattern of the second layer is carried by a semi-flexible plate of heat-stable polycarbonate material, constituting an intermediate pressure distribution layer, the plate being adhesively stuck to the fourth layer and to the
(Continued)

first layer, the peripheral spacer defining an air gap between the second and fourth layers.

20 Claims, 5 Drawing Sheets

(51) Int. Cl.
    *B32B 5/00*     (2006.01)
    *G01L 1/20*     (2006.01)
    *B32B 27/28*     (2006.01)
    *B32B 3/08*     (2006.01)
    *B32B 7/14*     (2006.01)
    *B32B 27/08*     (2006.01)
    *B32B 27/36*     (2006.01)
    *B32B 7/05*     (2019.01)
    *A61N 2/00*     (2006.01)
    *A61B 90/00*     (2016.01)

(52) U.S. Cl.
CPC ................. *B32B 7/05* (2019.01); *B32B 7/14* (2013.01); *B32B 27/08* (2013.01); *B32B 27/281* (2013.01); *B32B 27/285* (2013.01); *B32B 27/365* (2013.01); *G01L 1/205* (2013.01); *G01L 1/2287* (2013.01); *A61B 2090/064* (2016.02); *B32B 2250/24* (2013.01); *B32B 2255/10* (2013.01); *B32B 2307/202* (2013.01); *B32B 2307/308* (2013.01); *B32B 2307/4023* (2013.01); *B32B 2307/732* (2013.01); *B32B 2457/00* (2013.01); *B32B 2535/00* (2013.01)

(56) References Cited

U.S. PATENT DOCUMENTS

| | | |
|---|---|---|
| 9,421,392 B2 | 8/2016 | Reihl et al. |
| 2005/0234286 A1 | 10/2005 | Roehl et al. |
| 2006/0007172 A1 | 1/2006 | Baker et al. |
| 2009/0143907 A1 | 6/2009 | Demathelin et al. |

MAGNETIC STIMULATION DEVICE COMPRISING A FORCE-SENSING RESISTOR

The present invention relates to the field of magnetic stimulation (MS), in particular transcranial magnetic stimulation (TMS), and concerns more specifically a force sensor or FSR device compatible with magnetic stimulation coils used as medical devices for patient treatment or clinical investigations. The invention also encompasses a magnetic stimulation (MS), in particular a TMS, equipment using at least one such sensor or device.

Magnetic stimulation is a non-invasive electrostimulation technique where an operator applies a coil onto the body or the head of a patient and triggers a pulse of current, which create a focused magnetic field a few centimeters away from the coil surface. This technique is used for neurostimulation, known transcranial magnetic stimulation (TMS), or peripheral nerves stimulation.

The coil is usually a single copper winding, or a figure-of-eight shape containing copper windings. The size of a coil is roughly the size of a shoe: each of the two parts of the figure-of-eight measures approximately 70 mm in diameter. The coil is connected to a generator, which produces high intensity pulses of electrical current, which in turn produce high intensity pulses of magnetic field in the coil. The pulses are defined on per-application basis depending on the stimulation protocol, and their duration is usually less than a few milliseconds. The magnetic field goes through the skin of the patient and it creates small electrical currents in the area of the brain or the muscles where the coil is applied, according to the principle of magnetic induction. That electrical current in turn stimulates the electrical activity of the targeted part, with applications in medicine and neuroscience.

The electrical current generator can be connected to a master control system that supervises the stimulation protocol. This control system can be in the same housing as the generator, or in another one. When it is in the same housing, the whole system is usually referred as a stimulator system. When it is not the same system, the generator is driven by a dedicated device that can be a computer device, a navigation device, or a robot. The goal of these master devices is to configure the shape and intensity of the electrical pulse, and to trigger the generator with repetitive bursts or single shot pulse.

In order to maximize the intensity of the electrical current induced inside the body or patient's brain—and maximize its potential medical effect—it is important to eliminate the magnetic gap that can exist between the surface of the coil and the skin of the patient head. That magnetic gap can be due, for instance, to hair thickness or movement of the head during a session leading to a significant layer of air between the coil and the skin.

It has been proposed in the state of the art, for example in U.S. Pat. Nos. 8,177,702 and 9,421,392, to detect the proximity and location of a TMS coil using a flat sensor comprised of a membrane incorporating a 2D array of two-state switches (ON-OFF). The digital information delivered by this membrane is exploited to provide a location information to help positioning the stimulation coil.

Now, the structure and construction of such a membrane are complex and subject to (undetectable) mal-functioning. Furthermore, providing an accurate value of the total pressure applied is tricky due to the multiple partial contact sensors.

The basic idea of the invention consists in using a force sensing resistance (FSR) sensor in order to verify the existence and the quality of the contact of a magnetic stimulation coil with the body of a patient by monitoring the pressure between the coil and the skin.

More precisely, the proposed invention consists mainly in specific improvements to an FSR sensor or device so that it can be used for detecting and maintaining soft contact while doing magnetic stimulation on the body or the head of a patient.

Such a sensor consists, in a known construction, of a thin, flat and multilayered device, wherein the actuator or functional layers of said FSR device comprise the following stack of layers, successively from its top face to its bottom face:
  a first layer intended to be applied to an object;
  a second layer comprising a pattern or an area of force sensitive or resistive ink;
  a third layer comprising adhesive material, forming a peripheral spacer element;
  a fourth layer made of a flexible substrate with a printed conductive pattern of a force sensing circuit;
  a possible layer forming an adhesive surface on the bottom face.

Such a sensor construction allows to have a variable electrical resistance sensor when variable pressure is applied to it: the electrical resistance variation results from the conductive FSR ink touching more or less the printed circuit.

The principle of building standard FSR sensors is widely known and many suppliers have specific manufacturing processes to assemble on-purpose sensors depending on customer needs (see for example U.S. Pat. No. 7,113,179).

As the FSR technology is used traditionally in very demanding environments like the automotive industry, such sensors are known to be robust and have a long durability to repeated contacts.

Now, the known designs of FSR sensors do not provide an accurate measurement of the applied pressure when the object in contact is of a small size, i.e. when the contact area is small in comparison to the surface of the sensor.

Furthermore, no integrity or connection checking means, allowing to know whether or not the sensor is damaged (in particular in its sensitive area) and whether or not it is connected, are proposed in the state of the art related to such sensors.

It is an aim of the invention to propose a solution overcoming at least the main limitations of the state of the art solutions mentioned herein before and allowing the use of FSR sensors in the field of MS technology, more specifically as contact sensors for stimulation coil assemblies.

To reach this aim the invention proposes, in a first aspect, a FSR sensor or device of the type mentioned previously herein, namely an analog, hardware, thin and flat sensor, with a multilayered structure, compatible for use with a magnetic stimulation coil and configured and intended to be fixed to the active flat surface of a magnetic stimulation coil, in particular a TMS coil, assembly, said sensor or device being characterized in that the pattern or area of force sensitive or resistive ink of the second layer is printed onto and carried by a semi-flexible plate of heat-stable polycarbonate material, with a thickness less than 1 mm, constituting an intermediate pressure distribution layer between the first and the second layers, said plate being adhesively stucked, on the one hand, to the fourth layer with its face carrying the ink of the second layer through the peripheral body of the third layer, and, on the other hand, to the first layer, said peripheral body of the centrally hollow third layer defining or delimiting an air gap between said second and fourth layers.

The present invention also concerns, in another aspect, a magnetic stimulation (MS) or TMS equipment comprising at least one coil assembly, a generator delivering electrical signals to said at least one coil, a robotized or manually operated coil holding and positioning structure and a control system, equipment characterized in that said at least one coil assembly comprises, adhesively affixed on its or on each of its active surface(s), a flat FSR device as mentioned before, which is connected to an adapted electronic signal processing module or circuit, preferably associated with or forming part of the control system of the equipment.

The invention will be better understood and explained in more detail, by way of non-limiting embodiments, hereinafter, with reference to the attached drawings wherein.

Figure 1:
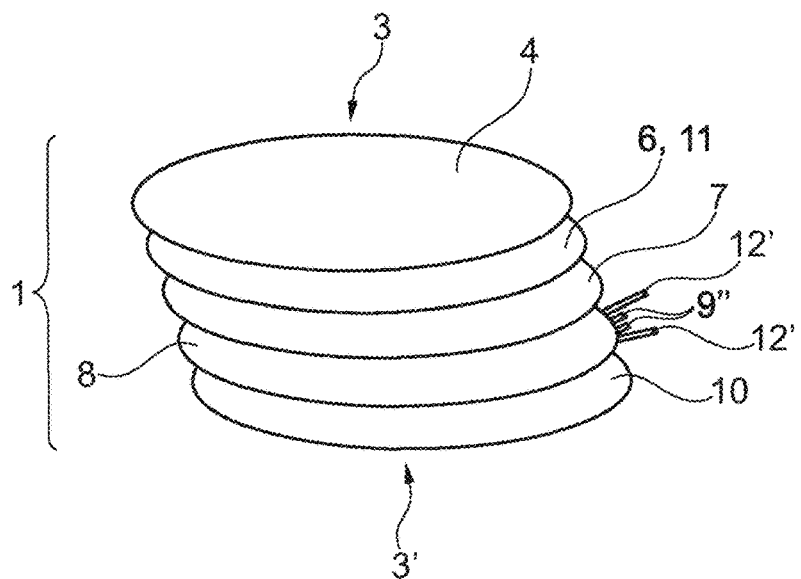
FIG. 1 is an exploded perspective view of a FSR device according to an embodiment of the invention (circular shape)
Figure 2:
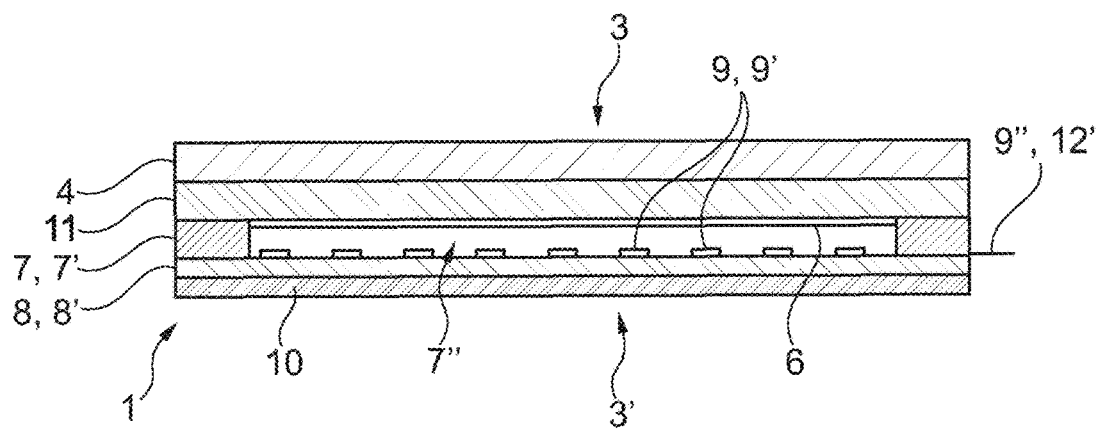
FIG. 2 is a sectional view of a FSR device as shown in FIG. 1, in the assembled state.
Figure 3:
FIG. 3 is a perspective view of the hollow third layer of the multilayered FSR device of FIGS. 1 and 2.

FIGS. 1, 2, 5A and 5B illustrate a thin and flat force-sensing resistor or FSR device 1, compatible with a magnetic stimulation coil and configured and intended to be fixed to the active flat surface 2' of a magnetic stimulation (MS), for example a transcranial magnetic stimulation (TMS) coil assembly 2.

The actuator or functional layers of said FSR device 1 comprise the following stack of layers 4, 6, 7, 8, 10, successively from its top or skin contact face 3 to its bottom or coil contact face 3':

a first layer 4 made of biocompatible flexible material intended to be applied to the skin of a patient 5;

a second layer 6 comprising of a pattern or an area of force sensitive or resistive ink;

a third layer 7 comprising adhesive material, forming a peripheral spacer element 7';

a fourth layer 8 made of a flexible heat-stable polycarbonate substrate 8' with a printed conductive pattern 9, 9' of a force sensing circuit;

a fifth layer 10 forming an adhesive surface on the bottom face 3'.

According to the invention, the pattern or area of force sensitive or resistive ink of the second layer 6 is printed onto and carried by a semi-flexible plate 11 of heat-stable polycarbonate material, with a thickness less than 1 mm, constituting an intermediate pressure distribution layer between the first layer 4 and the second layer, said plate 11 being adhesively stucked, on the one hand, to the fourth layer 8 with its face carrying the ink of the second layer 6 through the peripheral body 7' of the third layer 7, and, on the other hand, to the first layer 4, said peripheral body 7' of the centrally hollow third layer 7 defining or delimiting an air gap 7" between said second and fourth layers 6 and 8.

By providing an additional pressure distribution layer 11 in the form of a thin flexible plate, which is intimately and continuously (over its surface) stuck to the pressure impacted first layer 4, the pressure exerted by an object applied with a local contact to said first layer 4 is distributed to the second layer 6 by enlarging the surface of contact to said layer.

This feature is, for example in the field of TMS, of particular interest when an object of a smaller section than a head touches the first layer 4: this is the case for instance when the head of the patient 5 is equipped with electrodes (like EEG electrodes or NIRS electrodes) and the sensor 1 touches an electrode instead of the head.

Furthermore, this specific layer 11 advantageously cooperates with the single and continuous air gap chamber 7" delimited laterally by the hollow spacer element 7' to provide a sensor 1 whose exit signal (amplitude) is proportional to the applied pressure (on layer 4) and to the resulting deformation and contact between 6 and 9, 9'.

Figure 4:
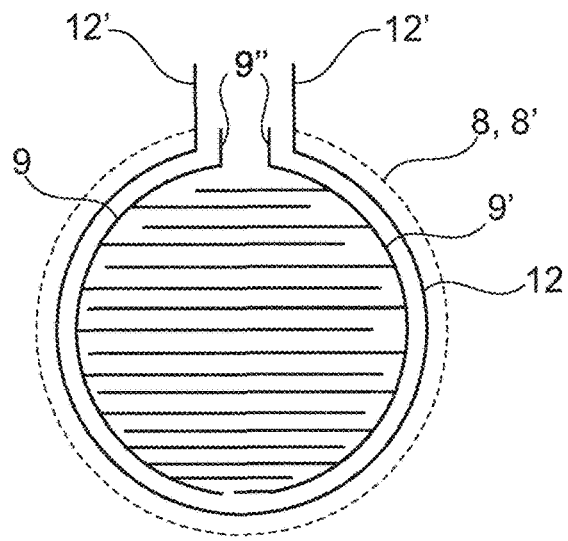
FIG. 4 is a top view of the fourth layer of the FSR device of FIGS. 1 and 2, showing its conductive pattern and line.

According to another important feature of the invention, and as shown in FIG. 4, the FSR sensor or device 1 comprises a control loop 12 extending around the conductive pattern 9, 9' of the fourth layer 8, along the peripheral edge of its substrate 8' and under the peripheral body 7' of the third layer 7.

As also shown on FIG. 4, the conductive line 12 forming the peripheral control loop and the two complementary components 9 and 9' forming the printed conductive pattern of the fourth layer 8, such as two interleaved combs, include respective electrical terminals 9", 12' for connection with an electronic signal processing module 13.

The integrity control loop 12 is positioned at the periphery of the fourth layer 8 so that it does not have any electrical connection with the internal region of said layer 8.

Being located in the periphery, that conductive line 12 will be isolated from the conductive ink of the second layer 6 thanks to the adhesive material of the peripheral body 7' of the layer 7.

As is apparent from the previous disclosure and the drawings, the sensor or device 1 has a multilayered constitution of various functional and/or structural mutually stacked layers which are adhesively assembled together (by the adhesive rear face of the first layer 4 and by the adhesive peripheral body 7' of the third layer 7).

In use, said sensor or device 1 is also glued through the fifth layer 10 to the active surface 2' of the coil assembly 2 and thus the borders of the device or sensor 1 may be subject to tearing, scratching, collision with external objects or underneath penetration of dust.

Assuming tearing, scratching, collisions to the border of the sensor 1, or penetration of dust damages the control loop 12, its conductivity would be broken, which can be measured in the associated electronic processing module 13. Also said control loop 12 allows to check whether or not the sensor or device 1 is properly connected.

Advantageously, the ring or frame shaped peripheral body 7' of the third layer 7 and the fifth layer 10 are made of double-sided adhesive tape.

Figure 5A:
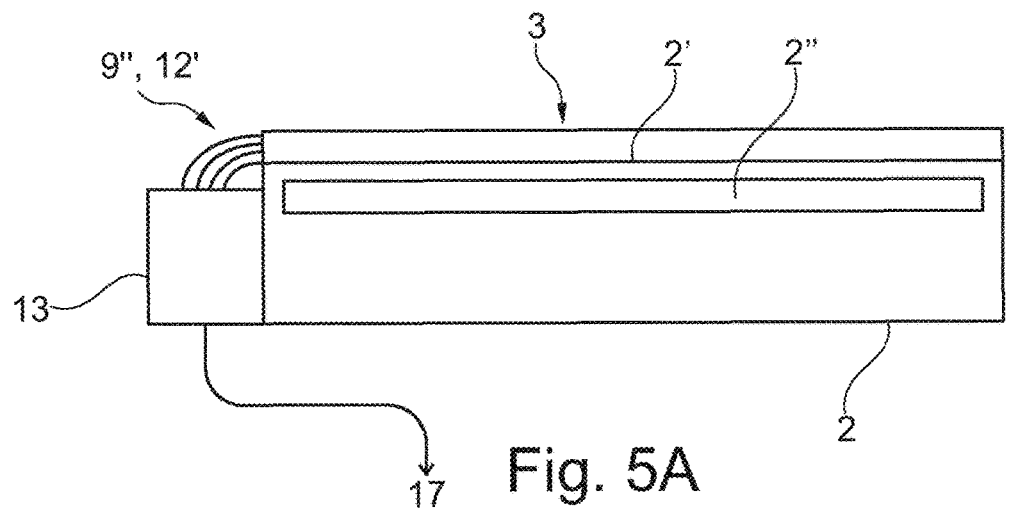
FIG. 5A is a sectional view of a magnetic stimulation coil assembly equipped with a FSR device according to a first embodiment of the invention.
Figure 5B:
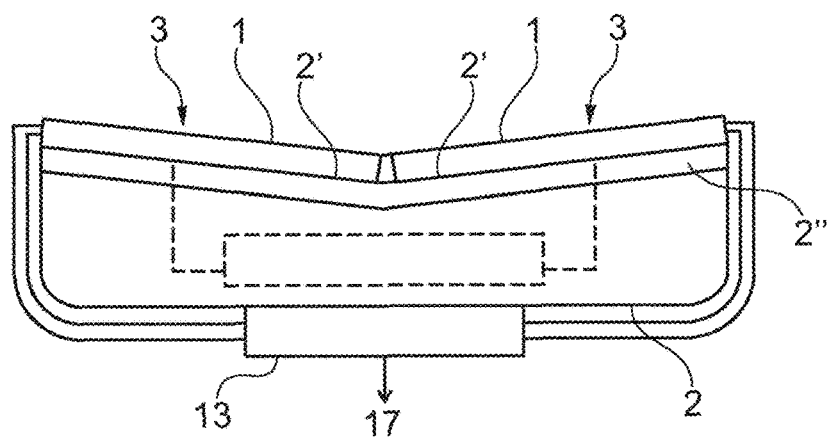
FIG. 5B is a sectional view of a magnetic stimulation coil assembly equipped with a double FSR device or two separate FSR devices according to a second embodiment of the invention.

According to a first embodiment of the invention, shown in FIGS. 5A and 5B, said sensor or device 1 is sized and configured to cover the entirety of the active surface 2' of the corresponding coil assembly 2 it is intended to be affixed to.

In a first alternative of this first embodiment, a sensor or device 1 with a single conductive area or pattern can be used to cover the whole single flat surface 2' of the coil assembly 2 (FIG. 5A).

In a second alternative of this first embodiment, in particular when the active surface 2' of the coil assembly 2 is comprised of at least two flat portions inclined to each other (FIG. 5B), the sensor or device 1 can show at least two conductive patterns or areas, each one of them associated with a corresponding surface portion.

Each portion of the active surface 2' may also be covered, completely or partially, by an independent sensor or device 1, dedicated to that portion.

According to a second embodiment of the invention, not shown on the attached drawings, the sensor or device 1 is sized and configured to cover a limited central area of the active surface 2' of the corresponding coil assembly 2 it is intended to be affixed to.

Of course, various designs of conductive patterns 9, 9' can be envisaged, as well as various shapes of the sensor or device (rectangular, in the form of an 8, circular, elliptic, . . . ) depending on the shape and the layout of the coil assembly 2, it is to be affixed to.

In a practical preferred construction of the invention, the sensor or device 1 has a total thickness of less than 1 mm, preferably around 0.90 mm.

For example, the constitutive layers can show the following individual thicknesses:

First layer 4: 0.25 mm (for example made of biocompatible resin, such as ULTEM 1000 (registered trademark)

Polycarbonate plate 11: 0.28 mm

Second layer 6 with FSR ink pattern or area (possibly also including a polymer film as supporting substrate for the printed ink)

Peripheral body 7' of third layer 7: 0.05 mm

Fourth layer 8 (including substrate 8' and printed conductive pattern 9, 9'—made of copper or silver): 0.13 mm Fifth surface adhesive layer 10: 0.05 mm.

Thus, the overall thickness of the sensor 1 is negligible and does not act as a magnetic gap itself compared to the dimensions of the magnetic field created outside of the coil, whose effective dimension is generally about 20 to 30 mm in a direction perpendicular to the coil.

One can describe the principle of measuring the contact of an object with the coil assembly 2 as follows, when a sensor or device 1 is present on the active face 2' of said coil:

when no object is applied to the first layer 4, free air in within chamber 7" of the third layer 7 isolates the resistive ink area of the second layer 6 from the conductive circuit 9, 9' of the fourth layer 8, giving the conductive circuit a constant overall resistance which can be measured at connections or terminals 9"';

when an object is applied to the first layer 4, free air in chamber 7" is suppressed displaced at the position of the contact, putting the resistive ink of the second layer 6 in contact with the conductive circuit 9, 9' of the fourth layer 8, decreasing the overall resistance of said layer 8 measured at connections or terminals 9"'.

If the size of the surface of the object in contact with the first layer 4 increases, more resistive ink will touch the conductive circuit, decreasing the resistance of the fourth layer 8 of a greater amount.

If the pressure applied by the object in contact increases, the resistance of the ink of the second layer 6 will decrease, decreasing further the resistance of the fourth layer 8 measured at terminals or connections 9"'.

Figure 7:
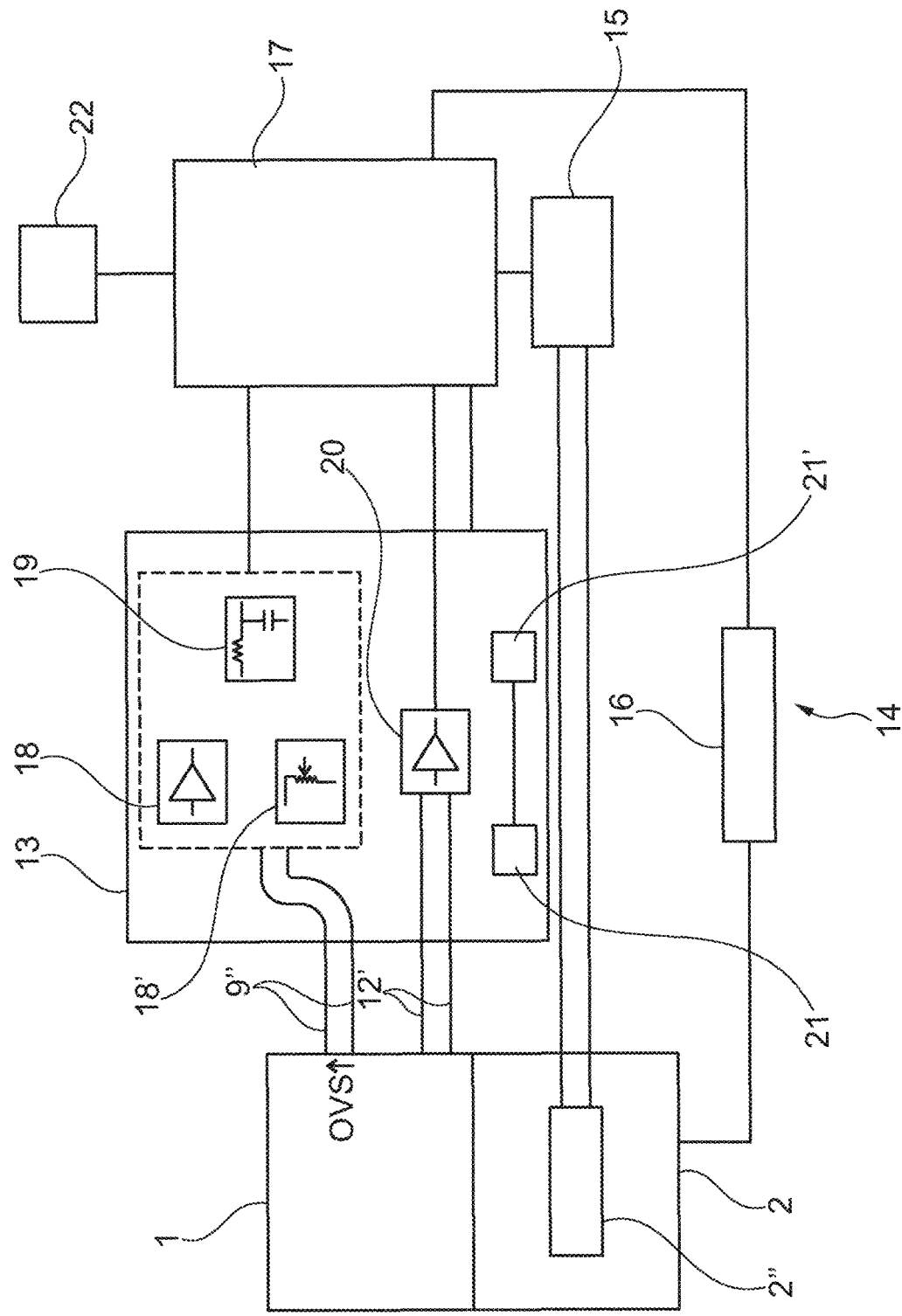

As illustrated on FIGS. 5A, 5B and 7, the FSR sensor or device 1 is connected to an electronic adapter or module 13 containing the signal processing boards. The housing of said module can be fitted close to the side of the magnetic stimulation coil assembly 2, within it (see dotted lines in FIG. 5B) or in another part that can be plugged to the sensor 1.

As the FSR sensor or device 1 is a variable resistance sensor, the electronics of the module 13 is meant to convert this variable resistance to a voltage signal or a digital data that can be read by the control system 17 of the magnetic stimulation equipment 14.

The electronics provides a constant current supply, preferably less than 1 mA, that goes through the FSR sensor 1. Setting a constant intensity in the sensor 1 allows to read a voltage that varies with the pressure applied to said sensor 1.

An alternative would be to set a constant voltage and to read an intensity that varies with the pressure applied to the sensor 1.

A more detailed description of the electronic module 13 is given hereinafter in relation to a practical embodiment of the invention and its constitutive components and functioning.

Figure 6A:
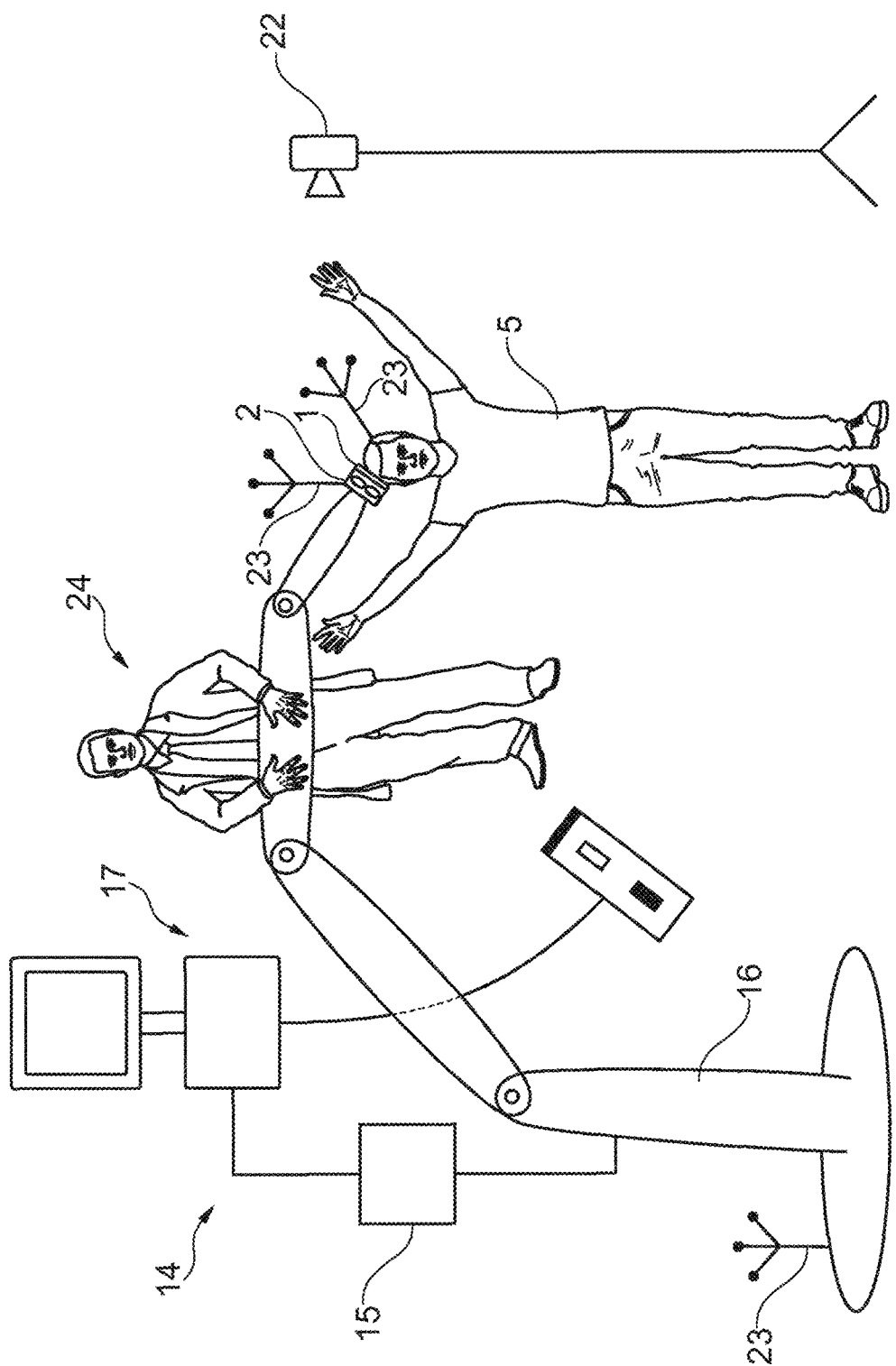
FIGS. 6A and 6B are schematic views of a magnetic stimulation equipment comprising a coil assembly as shown in FIG. 5A or in FIG. 5B, during a preliminary positioning phase (FIG. 6A) and during a following automatic treatment phase (FIG. 6B), and, FIG. 7 is a simplified functional drawing of magnetic stimulation equipment according to an embodiment of the invention.
Figure 6B:
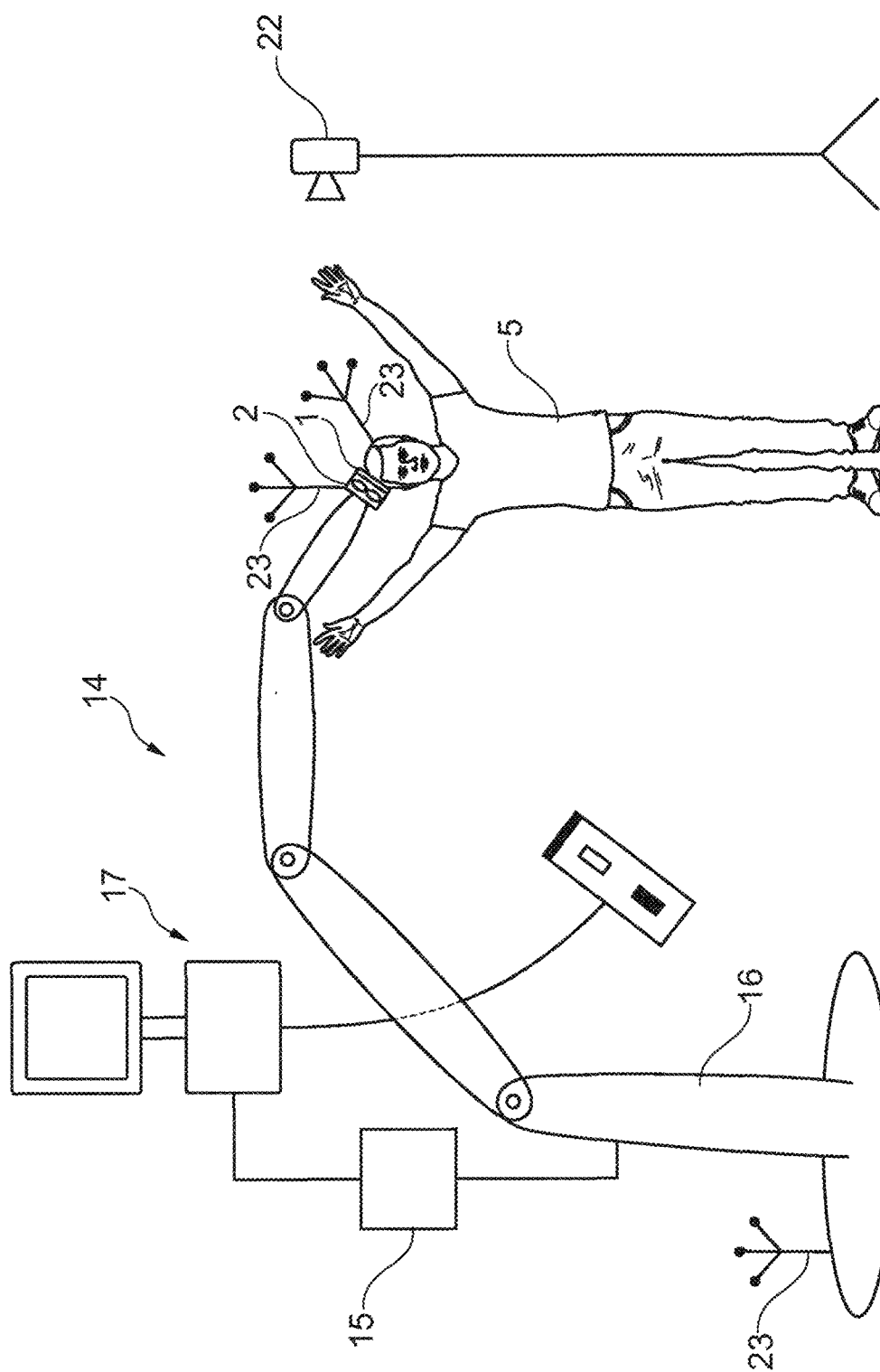

Said invention also encompasses, according to another aspect, and as shown on FIGS. 6A, 6B and 7, a magnetic stimulation, in particular TMS, equipment 14 comprising at least one stimulation coil assembly 2, a generator 15 delivering electrical signals to said at least one coil, a robotized or manually operated coil holding and positioning structure 16 and a control system 17.

Said equipment 14 is characterized in that said at least one coil assembly 2 comprises, adhesively affixed on its or on each of its active surface(s) 2', a flat FSR device 1 as described before which is connected to an adapted electronic signal processing module 13 or circuit, preferably associated with or forming part of the control system 17 of the equipment 14.

Said module 13 can be, as mentioned before, be located at or near the coil assembly 2, or being integrated within the control system 17.

In compliance with a feature of the invention, the signal processing module 13 comprises an operational amplifier based arrangement 18 able to inject a small current, typically less than 1 milliampere, into the printed conductive pattern 9, 9' of the fourth layer 8 and to measure the output voltage signal (OVS) indicative of the electrical resistance of the FSR device 1 connected to said module 13, this module 13 also including a potentiometer 18' to calibrate the sensitivity of the measure with a reference pressure applied on the first layer 4 of the device 1 and resistor, capacitor and diode means arranged to protect against over-current. Preferably, the output voltage OVS is saturated so as to avoid damage to the circuits.

According to another feature, the module 13 may comprise another operational amplifier based arrangement 19 able to detect whether or not said control loop 12 is damaged or disconnected by measuring its electrical resistance and to provide a corresponding information on that subject, for example as a voltage digital output, said arrangement 20 also incorporating resistor, capacitor and diode means to protect against over-current. So the magnetic stimulation pulse artefacts are filtered.

The module 13 is also connected to the terminals 12' of the control loop 12 of the FSR device 1 and comprises another operational amplifier based arrangement 19 able to detect whether or not said control loop 12 is damaged or disconnected by measuring its electrical resistance and to provide a corresponding information on that subject, for example as a voltage digital output, said arrangement 20 also incorporating resistor, capacitor and diode means to protect against over-current.

Preferably, the module 13 also comprises another operational amplifier based arrangement 19 able to detect whether or not said control loop 12 is damaged or disconnected by measuring its electrical resistance and to provide a corresponding information on that subject, for example as a voltage digital output, said arrangement 20 also incorporating resistor, capacitor and diode means to protect against over-current.

The non-volatile memory may comprise counters to store lifetime, saturated time and out-of-date time information concerning a considered FSR device 1 allowing to identify and to track said device 1 over its lifetime.

The control system 17 comprises software means to process the information provided by the signal processing module 13 associated with the at least one FSR device 1 and to determine whether the concerned coil assembly 2 touches the body of a patient 5 in a manner adequate for applying stimulation signals to the coil(s).

Advantageously, the information provided by the signal processing module 13, in the form of analog or digital voltage or pressure data, is compared by the control system 17 to threshold values, preferably to at least a predetermined minimum value and a predetermined maximum value.

When the pressure value is within the threshold values range, the control system 17 may alert the operator or imitate automatically a pulse sequence.

To that end, the equipment 14 may comprise visual and/or sound signaling or feedback means triggered by the control system 17 when the at least one coil assembly 2, or at least a portion of the active surface 2' of such an assembly 2, touches the body of the patient 5 with a soft force or pressure, for example when the pressure applied on the concerned FSR device 1 is within the range of 50 g/cm$^2$ to 500 g/cm$^2$.

As schematically shown on FIGS. 6A and 6B, the structure 16 which is holding and positioning the said at least one coil assembly 2 comprises a robotized arm with at least six degrees of freedom, or six axis robot, preferably of the man-machine interactive or collaborative type and controlled by the control system 17, which advantageously exploits the data provided by the at least one FSR device 1 associated with said at least one coil assembly 2, as feedback and command information.

In order to fully use the potential of the robotized arm 16, the equipment 14 may also comprise an image taking device 22, preferably an optical image taking device, linked to the control system 17 and delivering images, advantageously real time video images, allowing spatial location and tracking of the at least one coil assembly 2 by said control system 17.

Hereinafter, the invention is described in more detail by way of example and in relation with the FIGS. 1 to 7, in its constructive aspect as well as in its functional aspects.

First, under a practical aspect and as the TMS pulses create important artifacts in the electronics circuit due to change in the current, it is important to:
  saturate the maximum voltage that can be read to a maximum value so that the available range is 0 V-Vmax
  filter the measurements with a low pass filter 19 at a cutoff frequency so that stimulation artifacts do not affect the measurements. In the case of repetitive TMS coils, this is usually 3 kHz.

The electronic module 13 includes a potentiometer 18' allowing to adjust the voltage output OVS when a constant weight is applied to the sensor 1. The preferred sensibility is set to output a ⅕fifth range for a pressure of 200 gr/cm$^2$.

The sensibility is tuned on a per-sensor basis or per-batch, using a calibration method to ensure repeatability over a production batch, or for a wide range of sensors 1 of different shapes.

The control loop circuit 12 is checked by the electronic module 13 by measuring the resistance of the circuit and ensuring the value is in the order of a few Ohms.

In case the sensor 1 is not plugged, or the surface has tearing and scratches, the resistance will increase or even become an open circuit, which will be detected by the electronics.

The micro-controller 21, using for example a Microchip PIC controller, is used to convert the analog signals of the contact areas to a numerical value stored as a integer or a float value in the volatile memory 21' of the controller 21. The analog value is converted to a unitless value, but a table can be used to calibrate this unitless values to pressure values in gr/cm$^2$.

The control loop digital value is also converted to a Boolean value in the memory to report if the sensor 1 is connected (no wire broken) and not damaged.

The values are updated at a refresh rate that is compatible with the low-pass filtering used to remove the magnetic pulses artefacts, for example at twice the period of the cutoff period of the analog low pass filter 19.

The controller 21 can store in a non-volatile memory 21' a unique identification number and lifetime usage of a given sensor 1 so that the control system 17 can inform the user about: number of hours the sensor has been in use (lifetime), how much time it has been saturated, or if it is out-of-date and should not be used anymore.

The lifetime counters are updated at the same rate as the input values are read and they are written into a non-volatile memory.

The communication between the micro-controller 21 and the control system 17 is done, for example, by means of:
  a serial bus like: RS232, RS485, USB
  a parallel bus like: CAN Bus, Ethernet, Ether CAT buses.

The micro-controller 21 contains a software that is used to configure said micro-controller 21 and implements the above functionalities and protocol to retrieve data.

The control system 17 uses the pressure information from the sensor 1 to inform the user about the intensity of the pressure applied to the sensor 1 so that the contact is soft and painless for the patient 5.

It also reports the connection status of the sensor 1 and its integrity (control loop 12).

Using several areas of contact, it can moreover inform the user whether the central part of the active surface of the coil assembly 2 is in contact.

This information can be displayed either by lights on the control system 17, by a specific display or screen, or by emitting characteristic sounds like a repetitive short beep when there is no contact, no sound when enough contact is applied, or a continuous beep if contact is too much.

The pressure information is split into levels to segment the amount of force applied by the coil assembly 2 to the body of the patient 5.

This allows the control system 17 to detect the desired level of contact between body 5 and coil assembly 2:
  a zero level, or null contact, if no pressure or electrical noise is detected. For example, pressure is below 50 gr/cm$^2$.

a level 1, or light contact, if coil assembly 2 touches the body without applying enough pressure to avoid air gap due to e.g. hair or head cap. For example, pressure is between 50 gr/cm^2 and 150 gr/cm^2.

a level 2, or smooth and comfortable contact, which means the pressure is enough to avoid an air gap, but the skin. For example, pressure is between 150 gr/cm^2 and 300 gr/cm^2.

a level 3, or excessive contact, if pressure is higher than an acceptable feeling. For example, pressure is between 300 gr/cm^2 and 1000 gr/cm^2.

a level 4, or excessive or saturated contact. For example, pressure is more than 1000 gr/cm^2.

The above example values are given for a control system 17 that manages a head contact, and values may be optimized for another part of the body.

The pressure currently applied is converted into the previous by mentioned levels and a visual signal or a sound signal warns the user about contact level being too low (0 or 1) or too high (3 or 4).

The control system 17 can use the contact level to condition the triggering of a magnetic pulse.

By using a sensor 1 equipped with a control loop circuit 12 and connected to an electronics control module 12, the control system 17 can detect whether the control loop 12 is broken (open-circuit) meaning either the sensor is damaged, or a wire is broken or disconnected.

This information can be used to inform the user about a failure in either the internal cabling, or a defective sensor 1 that needs to be replaced or repaired.

In case a micro-controller 21 is used, a unique identification number can be used to track the usage of the sensor 1 which can be used to track the coil usage.

The lifetime counters can be retrieved so that the user can be informed about usage statistics and whether the considered sensor becomes out-of-date.

The invention also concerns a method for transcranial magnetic stimulation (TMS) treatment of a patient 5 using an equipment 14 as described before, characterized in that it comprises at least the two successive operational phases of:

first positioning the TMS coil assembly 2 in contact with the targeted area of the body of the patient 5, by manually guiding the robotized holding and positioning arm 16 functioning in a collaborative mode and by exploiting the data provided by the FSR device 1 associated with said coil assembly 2 and once the right positioning is reached, switching the equipment 14 into an automatic treatment mode, according to a predetermined treatment protocol, wherein a target locking procedure is applied for maintaining automatically the TMS coil assembly 2 in the right position with respect to the targeted area, by exploiting simultaneously imaging data of the operative scene from an image taking device 22 and pressure data from the FSR device 1 associated with said concerned coil assembly 2.

These two phases are schematically illustrated on FIGS. 6A and 6B. On these figures, the robotized arm 16, the patient 5 and the coil assembly 2 are equipped with fiducial markers 23, visible on optical imaging means, but preferably also by other imaging means (RMI, CT scan, . . . ). The patient 5 can be in a seated position or lying on a medical bed (not shown).

The operator 24 is only present and active in the collaborative positioning phase of the coil assembly 2 (FIG. 6A).

As an alternative to the robotized arm 16 of FIGS. 6A and 6B, the structure holding and positioning the coil assembly 2 may be a robotic device as disclosed in WO-A-2006/035143.

In summary, the present invention concerns primarily a force sensor 1, its signal processing electronics used to measure a contact between the skin of a patient body 5 and a magnetic stimulation coil 2" in order to ensure soft and permanent contact while stimulating.

More specifically, the sensor 1 is designed to be compatible with pulse-based external magnetic stimulation procedures, specifically in the case of transcranial magnetic stimulation (TMS) and peripheral nerves stimulation coils. The invention is meant to be used with standard magnetic stimulation equipment's and stimulation coils, either in robotized procedure or for manual operations.

The force sensor assembly 1 consists in a special arrangement of force sensing layers 4, 6, 8, 9, 9' and an associated signal processing electronics 13 specifically designed to filter magnetic pulses disturbance and allows the control system 17 of the equipment 14 to inform the user in real time whether the concerned coil is rightly applied or not.

The conductive pattern of the FSR sensor 1 can be designed to cover any kind of shape.

In a simplified version of the invention, the whole face of the coil assembly 2 can be covered by a force sensor 1 with only one area. This allows the control system to be aware of the coil coming in contact with the body or the head, regardless of the position of the contact within the area. Indeed, the position of contact can be measured without the force sensor, using an external 3D measurement system 22 like a camera, a passive mechanical arm equipped with position sensors, a robot handling the coil, or a neuro-navigation system.

An alternative is to have only a small sensor 1 which covers only the central part of the coil 2", where the stimulation is supposed to be applied, so that the force sensor can be used to measure the position of contact when no external 3D measurement system is available to ensure correct positioning of the coil 2".

The inventors have performed experiments with embodiments of the FSR technology sensor 1 on commercial coils 2" and stimulators 14, with full intensity stimulation protocols. The electrical current used to measure the electrical resistance was below 1 mA. The magnetic field disturbance on the output signal was seen as small variations in voltage, which duration is less than the pulse duration. This disturbance was easily filtered by a low-pass filter 19 with adapted capacitors and resistors whose values were computed so that cutoff frequency (or period) was below the magnetic pulse duration. For example, the maximum pulse duration was 1 ms, so the filter 19 was tuned to 1 kHz cutoff frequency. The formula used for the selection of the components was the classical formula for R*C time constant: Cutoff frequency=1/(2*Pi*R*C), or Cutoff Period=2*Pi*R*C.

To reduce footprint of the electronics, the capacitors and resistors are surface mounted components, whose value are taken to be about C=1 . . . 100 nF, and R=0.1 . . . 100 kOhms.

The invention is of course not limited to the embodiments, alternatives and features mentioned herein before, but also aims to encompass technical equivalents to the subject matter of the attached claims.

The invention claimed is:

1. A thin and flat FSR (force sensing resistance) device, compatible with a magnetic stimulation coil and configured to be fixed to an active flat surface of a magnetic stimulation coil assembly, wherein functional layers of said FSR device comprise:

layers, successively from a top or skin contact face to a bottom or coil contact face including:

a first layer made of biocompatible flexible material intended to be applied to the skin of a patient;

a second layer comprising a pattern or an area of force sensitive or resistive ink printed onto a semi-flexible polycarbonate plate;

a third centrally hollow layer comprising adhesive material and forming a peripheral spacer element between the second layer and a fourth layer;

the fourth layer made of a flexible heat-stable polycarbonate substrate with a printed conductive pattern of a force sensing circuit; and a fifth layer forming an adhesive surface on the bottom face, wherein the printed pattern or area of force sensitive or resistive ink of the second layer is carried by a semi-flexible polycarbonate plate of heat-stable polycarbonate material, with a thickness less than 1 mm, said semi-flexible polycarbonate plate constituting an intermediate pressure distribution layer between the first layer and the second layer, wherein said semi-flexible polycarbonate plate is adhesively stuck both with said face carrying the pattern or area of force sensitive or resistive ink of the second layer and through the peripheral spacer element of the third layer, to the fourth layer and, as well as intimately and continuously to the first layer, and wherein said peripheral spacer element of the centrally hollow third layer defines or delimits an air gap between said second and fourth layers.

2. The FSR device according to claim 1, further comprising a control loop extending around the conductive pattern of the fourth layer, along a peripheral edge of said flexible heat-stable polycarbonate substrate and under the peripheral spacer element of the third layer.

3. The FSR device according to claim 2, wherein the control loop and the conductive pattern forming a printed conductive pattern of the fourth layer, include respective electrical terminals for connection with an electronic signal processing module.

4. The FSR device according to claim 1, wherein a peripheral body of the third layer and the fifth layer are in a ring or frame shape and are made of double-sided adhesive tape.

5. The FSR device according to claim 1, wherein said FSR device is sized and configured to cover an entirety of the active surface of the magnetic stimulation coil assembly said FSR device is intended to be affixed to.

6. The FSR device according to claim 1, wherein said FSR device is sized and configured to cover a limited central area of the active surface of the magnetic stimulation coil assembly said FSR device is intended to be affixed to.

7. A magnetic stimulation equipment comprising:
at least one said magnetic stimulation coil assembly,
a generator delivering electrical signals to said magnetic stimulation coil,
a robotized or manually operated coil holding and positioning structure and
a control system, wherein said at least one magnetic stimulation coil assembly comprises, adhesively affixed on said active surface thereof, said flat and thin FSR device according to claim 1 which is connected to an adapted electronic signal processing module or circuit.

8. The magnetic stimulation equipment according to claim 7, wherein the signal processing module comprises an operational amplifier based arrangement able to inject a small current, less than 1 milliampere, into the printed conductive pattern of the fourth layer and to measure an output voltage signal indicative of an electrical resistance of the FSR device connected to said signal processing module, said signal processing module also including a potentiometer to calibrate a sensitivity of a measure with a reference pressure applied on the first layer of the device and resistor, capacitor and diode means arranged to protect against over-current.

9. The magnetic stimulation equipment according to claim 7, wherein the signal processing module comprises a low-pass filter, said low-pass filter processing an output voltage signal and having a cut-off period at least twice a maximum duration of an expected magnetic pulse emitted by the at least one magnetic stimulation coil assembly.

10. The magnetic stimulation equipment according to claim 8, wherein the signal processing module is also connected to terminals of a control loop of the thin and flat FSR device and comprises a second operational amplifier based arrangement able to detect whether or not said control loop is damaged or disconnected by measuring an electrical resistance of said control loop and to provide a corresponding information on said electrical resistance including a voltage digital output, said second arrangement also incorporating resistor, capacitor and diode means to protect against over-current.

11. The magnetic stimulation equipment according to claim 7, wherein the signal processing module also comprises a micro-controller and associated software able to convert analog measurement values into digital data and also volatile and non-volatile memories able to store said data and which are accessible via a bus or a serial connection.

12. The magnetic stimulation equipment according to claim 11, wherein the non-volatile memory of said volatile and non-volatile memories comprises counters to store lifetime, saturated time and out-of-date time information concerning said flat and thin FSR device allowing to identify and to track said flat and thin FSR device over its lifetime.

13. The magnetic stimulation equipment according to claim 7, wherein the control system comprises software means to process information provided by the signal processing module associated with the at least one thin and flat FSR device and to determine whether said at least one magnetic stimulation coil assembly touches a body of the patient in a manner adequate for applying stimulation signals to said magnetic stimulation coil.

14. The magnetic stimulation equipment according to claim 13, wherein the information provided by the signal processing module is in the form of analog or digital voltage or pressure data, and is compared by the control system to threshold values.

15. The magnetic stimulation equipment according to claim 7, further comprising visual and/or sound signaling or feedback means triggered by the control system when the at least one magnetic stimulation coil assembly, or at least a portion of the active surface, touches a body of the patient with a soft force or pressure when pressure said flat and thin FSR device is within a range of 50 g/cm$^2$ to 500 g/cm$^2$.

16. The magnetic stimulation equipment according to claim 7, wherein the holding and positioning structure said at least one magnetic stimulation coil assembly comprises a robotized arm with at least six degrees of freedom, or a six axis robot, that exploits data provided by the at least one flat and thin FSR device, as a feedback and command information.

17. The magnetic stimulation equipment according to claim 7, further comprising an image taking device linked to the control system and delivering images in real time video images, allowing a spatial location and tracking of the at least one magnetic coil assembly by said control system.

18. The magnetic stimulation equipment of claim 9, wherein the low-pass filter is analog.

19. The magnetic stimulation equipment of claim 18, wherein the low-pass filter comprises passive components.

20. A method for transcranial magnetic stimulation treatment of a patient using an equipment according to claim 16 and having an image taking device linked to the control system and delivering images, allowing spatial location and tracking of the at least one coil assembly by said control system, said method comprising at least two successive steps of:

first positioning the at least one magnetic stimulation coil assembly in contact with a targeted area of the body of the patient, by manually guiding the holding and positioning structure functioning in a collaborative mode and by exploiting the data provided by the flat and thin FSR device, and, once the positioning is reached, switching the equipment into an automatic treatment mode, according to a predetermined treatment protocol, wherein a target locking procedure is applied for maintaining automatically the at least one magnetic stimulation coil assembly in a right position with respect to the targeted area of the body, by exploiting simultaneously imaging data of an operative scene from an image taking device and pressure data from the flat and thin FSR device.

* * * * *